United States Patent
Yepez et al.

(10) Patent No.: US 6,294,387 B1
(45) Date of Patent: Sep. 25, 2001

(54) METHOD OF DETERMINING THE CORROSIVENESS OF NAPHTHENIC ACID IN CRUDE OIL REFINERY STREAMS

(75) Inventors: Omar Yepez, Edo Miranda; Jose Vera, Caracas, both of (VE)

(73) Assignee: Intevep, S.A. (VE)

( * ) Notice: Subject to any disclaimer, the term of this patent is extended or adjusted under 35 U.S.C. 154(b) by 0 days.

(21) Appl. No.: 09/275,528

(22) Filed: Mar. 24, 1999

(51) Int. Cl.⁷ .......................... G01N 31/00; G01N 31/22
(52) U.S. Cl. .................... 436/6; 436/151; 422/53
(58) Field of Search ................... 436/6, 151; 422/53

(56) References Cited

U.S. PATENT DOCUMENTS

| | | | |
|---|---|---|---|
| 2,679,752 | * 7/1954 | Metler | 73/104 |
| 4,238,298 | * 12/1980 | Tsuru et al. | 204/1 |
| 4,808,538 | * 2/1989 | Roffey et al. | 436/6 |
| 5,630,964 | * 5/1997 | Babaian-Kibala et al. | 252/389.23 |

OTHER PUBLICATIONS

"Predicting Crude Oil Corrosivity: Effects of Velocity, Interactions of Crude Oil Composition, Temeprature and Alloying". Kane, Russell D, Mar. 1992.*

* cited by examiner

*Primary Examiner*—Jill Warden
*Assistant Examiner*—LaToya I. Cross
(74) *Attorney, Agent, or Firm*—Bachman & LaPointe, P.C.

(57) ABSTRACT

A method for determining corrosiveness of naphthenic acid in a fluid includes the steps of: providing a fluid containing naphthenic acid; providing iron powder having a surface area of at least about 0.01 $m^2/g$; contacting the fluid and the powder for a period of time so as to provide a portion of the iron as dissolved iron dissolved in the fluid; and measuring iron concentration of the fluid containing the dissolved iron, so as to provide a measure of corrosion potential of the naphthenic acid over the period of time.

19 Claims, No Drawings

METHOD OF DETERMINING THE CORROSIVENESS OF NAPHTHENIC ACID IN CRUDE OIL REFINERY STREAMS

BACKGROUND OF THE INVENTION

The invention relates to a method for determining the corrosiveness of naphthenic acid contained in crude oils and refinery streams.

The corrosiveness of various components in crude oil and refinery streams is a real problem in that excessively corrosive components in such streams can destroy the distillation units in the refinery and other equipment as well One widely accepted method for representing the corrosiveness of a crude oil and/or refinery stream is the total acid number (TAN), which is determined as a number of milligrams of KOH per gram of material in question. It has been found, however, that total acid number is not an accurate indicator of corrosiveness of the crude oil and/or refinery stream in question, since acidity is not necessarily correlated directly with corrosiveness.

The conventional method to measure naphthenic acid corrosiveness is by means of placing coupons in the corrosive medium for a given time at the relevant temperature and pressure, according to "tandard Practice for Preparing, Cleaning, and Evaluating Corrosion Test Specimens", G1-90 and "Standard Guide for Corrosion Test in High Temperature or High Pressure Environment, or Both", G111-97, in Volume 03.02; Wear and Erosion; Metal Corrosion, of the 1998 Annual Book of ASTM Standards, Section 3:Metals Test Methods and Analytical Procedure".

An alternative method for measuring naphthenic acid corrosiveness is a weight loss measuring method disclosed in a publication entitled "Naphthenic Acid Corrosion in a Refinery Setting", By Babaian-Kibala E., et al., presented as paper 631 in the NACE International Annual Conference, Houston Tex., 1993.

These weight loss methods measure the corrosion as a total event and they are not capable of distinguishing between the corrosion processes caused by sulfur and naphthenic acids. Since the corrosion product of the naphthenic acid attack is soluble, Babaian-Kibala E., et al., measured the weight of the corrosion film on a steel coupon in units of $mg/cm^2$, which is the weight of corrosion product, and the total weight loss in mils per year, which is the corrosion rate. From this data they calculated a ratio of corrosion rate to corrosion product. If this ratio is less than 10, they state that the naphthenic acid contribution is little or non-existent. However, if the ratio exceeds 10, then naphthenic acid is said to have made a significant contribution to the corrosion process. The method does not work well with crude oils because during the test the crude oil tends to form a coke layer together with a corrosion film on the coupon surface. This results in errors when measuring the corrosion film weight.

Considering the foregoing, it is clear that the need remains for a simple, reliable and effective method for measuring the corrosiveness of naphthenic acid contained in a fluid such as crude oils or refinery streams.

It is therefore the primary object of the present invention to provide a method whereby corrosiveness of naphthenic acid can readily be determined.

It is a further object of the present invention to provide such a method wherein required materials are readily available.

It is a still further object of the present invention to provide such a method which can readily be incorporated for measurements carried out in the field, or in laboratories and the like.

Other objects and advantages of the present invention will appear hereinbelow.

SUMMARY OF THE INVENTION

In accordance with the present invention, the foregoing objects and advantages have been readily attained.

According to the invention, a method is provided for determining corrosiveness of naphthenic acid in a fluid, which method comprises the steps of: providing a fluid containing naphthenic acid; providing iron powder having a surface area of at least about 0.01 $m^2/g$; contacting said fluid and said powder for a period of time so as to provide a portion of said iron as dissolved iron dissolved in said fluid; and measuring iron concentration of said fluid containing said dissolved iron, so as to provide a measure of corrosion potential of said naphthenic acid over said period of time.

The method may be carried out at a known temperature, preferably at a range of known temperatures, so as to provide said measure of corrosion potential at various temperature.

In accordance with the present invention, the use of particulate or powder form iron ($Fe^0$) having high surface area advantageously allows for maintaining a high molar ratio of iron to naphthenic acid so that the naphthenic acid is the limiting factor of the reaction, and a good measurement of corrosiveness can thereby be obtained.

DETAILED DESCRIPTION

The invention relates to a method for determining corrosiveness of naphthenic acid in a fluid. Typical fluids which can advantageously be measured in accordance with the present invention include crude oils, refinery streams and the like. Such streams typically contain naphthenic acid which can be corrosive to critical equipment used in the distillation process.

In accordance with the present invention, examples of typical refinery streams which may be treated include but are not limited to atmospheric distillates, vacuum distillates and the like. Other hydrocarbon streams which can be tested using the method of the present invention include a wide variety of crude oils, heavy oils, light oils and the like. The method of the present invention advantageously allows for measuring the corrosiveness of naphthenic acid contained in the fluid.

In accordance with the present invention, a sample of fluid to be tested is obtained, for example from a refinery stream or other hydrocarbon stream, or as a fixed sample or the like.

In accordance with the present invention, the stream or sample is mixed with a powder or particulate iron ($Fe^0$) having a high surface area, preferably under an inert atmosphere and at expected reaction temperatures or conditions which are desired to be evaluated for corrosiveness. Under such conditions, a portion of the high surface area iron powder reacts with the fluid so as to become dissolved (as $Fe^{+2}$) in the organic phase, and a remaining portion is present as a solid ($Fe^{\circ}$)

In accordance with the present invention, the solid non-reacted iron is then removed through homogenizing and filtering the resulting mixed product. The dissolved iron concentration in the remaining organic phase is then measured using well known and conventional methods.

The velocity or corrosiveness of the naphthenic acid is then readily determined from the measured iron concentration present in the organic phase, typically as iron naphthanate, over the time during which the powder and stream were contacted.

This corrosiveness is preferably determined and provided in terms of reaction rate units and/or [Fe] ppm/hr.

In accordance with the present invention, the iron powder to be mixed is preferably a high surface area iron powder, preferably having a surface area of at least about 0.01 $m^2/g$, more preferably between about 0.05 and 2 $m^2/g$ and most preferably between about 0.1 and about 1 $m^2/g$. In addition, the powder preferably has an average particle size of less then or equal to about 50 $\mu$m.

The iron powder is preferably mixed with the stream or sample to be evaluated in amounts sufficient to provide a molar ratio of iron to naphthenic acid in the stream of at least about 1:2, and preferably greater than about 80:1. In accordance with the present invention, it has been found that this step advantageously provides for the naphthenic acid to be the limiting factor in the reactions which take place, thereby providing an accurate and reliable measurement of the actual corrosiveness of such naphthenic acid. This is in distinction to conventional methods which rely upon the unreliable total acid number (TAN), and/or the rate of weight loss of solid carbon steel coupons.

The iron powder and the stream to be measured in accordance with the present invention are preferably contacted by mixing sufficiently to provide a substantially homogeneous mixture of iron powder and the stream, and the time of contact is monitored. Following a desired time, as set forth above, the mixture will contain one portion of iron as solid non-reacted iron ($Fe^{\circ}$), while another portion of iron ($Fe+^2$) will be dissolved into the organic phase, typically as iron naphthanate.

The organic phase containing both solid non-reacted iron and reacted dissolved iron concentration is then treated through conventional homogenizing and filtering steps so as to separate and remove the solid non-reacted iron which can advantageously be recycled for future use. The remaining organic phase or stream is then measured for dissolved iron concentration using conventional methods such as, for example, the induced coupled plasma (ICP) method.

Corrosiveness can vary with temperature, and it is therefore preferred to carry out the contacting or mixing step at a known temperature, preferably at a range of known temperatures, whereby the measure of corrosiveness is correlated to corrosiveness at the particular temperature. In this manner, a range of corrosiveness values can be provided for the range of temperatures.

As set forth above, the contacting or mixing step is preferably carried under an inert atmosphere such as nitrogen or argon, for example. This atmosphere is inert with respect to the iron powder so as to advantageously avoid oxidation of same. Of course, other types of iron inert atmospheres could be used.

As set forth above, it should be appreciated that the method of the present invention provides a direct measure of the corrosiveness of naphthenic acid as desired. This method may suitably be used to evaluate such corrosiveness in fluids or streams having a total acid number of between about 0 and about 200 mgKOH/g. Further, the method of the present invention is particularly advantageous for use in treating fluids such as a 50° C.–500° C. cut from a refinery side stream.

It should also be appreciated that the method of the present invention is carried out using simple particulate or powdered iron, which is readily available and therefore contributes to the economic value of the present invention.

Finally, the method provides for measurements with a very high degree of accuracy and repeatability, which can be carried out in virtually any desired location.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed:

1. A method for determining corrosiveness of naphthenic acid in a fluid, comprising the steps of:

providing a fluid containing naphthenic acid;

providing iron powder having a surface area of at least about 0.01 $m^2/g$;

contacting said fluid and said powder for a period of time so as to react a portion of said iron with the naphthenic acid to form iron naphthenate which is soluable in said fluid; and measuring iron concentration of the iron naphthenate in said fluid containing iron, so as to provide a measure of corrosion potential of said naphthenic acid over said period of time.

2. A method according to claim 1, wherein said iron powder has an average particle size of less than or equal to about 50 $\mu$m.

3. A method according to claim 1, wherein said contacting step comprises contacting said powder and said fluid at a molar ratio of iron to naphthenic acid in said fluid of at least about 1:2.

4. A method according to claim 1, wherein said contacting step comprises contacting said powder and said fluid at a molar ratio of iron to naphthenic acid in said fluid of at least about 80:1.

5. A method according to claim 1, wherein said contacting step further provides a remaining portion of said iron as solid non-reacted iron in said fluid, and further comprising the step of removing said solid non-reacted iron before said measuring step.

6. A method according to claim 5, wherein said step of removing said solid non-reacted iron comprises homogenizing and filtering said fluid whereby said solid non-reacted iron is separated from said fluid.

7. A method according to claim 1, wherein said contacting step comprises mixing said powder and said fluid so as to provide a substantially homogeneous mixture of said powder and said fluid.

8. A method according to claim 1, wherein said contacting step is carried out under an inert atmosphere.

9. A method according to claim 1, wherein said fluid comprises a fluid stream.

10. A method according to claim 1, wherein said fluid comprises a hydrocarbon.

11. A method according to claim 1, wherein said fluid is a refinery stream.

12. A method according to claim 11, wherein said refinery stream is selected from the group consisting of atmospheric distillates, vacuum distillates and mixtures thereof.

13. A method according to claim 1, wherein said fluid is a crude oil.

14. A method according to claim 13, wherein said crude oil is selected from the group consisting of heavy oil, light oil and combinations thereof.

15. A method according to claim 1, wherein said fluid is a 50° C.–500° C. cut from a refinery side stream.

16. A method according to claim 1, wherein said fluid has a total acid number (TAN) of between about 0 and about 200 mg/KOH/g.

17. A method according to claim 1, wherein said contacting step is carried out at a known temperature, and said measure of corrosion potential is provided for said known temperature.

18. A method according to claim 1, wherein said iron powder has a surface area of between about 0.05 and about 2 $m^2/g$.

19. A method according to claim 1, wherein said powder is present in an amount sufficient to react all of the naphthenic acid in the fluid.

* * * * *